United States Patent [19]
Wun

[11] Patent Number: 5,849,703
[45] Date of Patent: Dec. 15, 1998

[54] PRE-FORMED ANTICOAGULANT HEPARIN/ TFPI COMPLEXES

[75] Inventor: Tze-Chein Wun, St. Louis, Mo.

[73] Assignee: G. D. Searle & Co., Chicago, Ill.

[21] Appl. No.: 661,240

[22] Filed: Jun. 10, 1996

Related U.S. Application Data

[63] Continuation-in-part of Ser. No. 453,937, May 30, 1995, which is a continuation-in-part of Ser. No. 166,186, Dec. 13, 1993, abandoned, which is a continuation of Ser. No. 573,083, Aug. 27, 1990, abandoned.

[51] Int. Cl.$^6$ .................. A61K 38/57; A61K 31/725
[52] U.S. Cl. .................. 514/12; 514/21; 530/395
[58] Field of Search .................. 514/12, 21; 530/395

[56] References Cited

U.S. PATENT DOCUMENTS

| | | | |
|---|---|---|---|
| 4,379,142 | 4/1983 | Port et al. | 424/101 |
| 4,966,852 | 10/1990 | Wun et al. | 435/235 |
| 5,212,091 | 5/1993 | Diaz et al. | 435/69.6 |
| 5,276,015 | 1/1994 | Khouri | 514/12 |
| 5,466,783 | 11/1995 | Wun et al. | 530/380 |

FOREIGN PATENT DOCUMENTS

| | | | |
|---|---|---|---|
| 91/19514 | 12/1991 | WIPO | A61K 37/64 |

OTHER PUBLICATIONS

Novotny et al., J. Biol. Chem. 264, 18832–18837 (1989).
Wun et al., J. Biol. Chem.—265, 16096–16101 (1990).
Wun et al., J. Biol. Chem. –263, 6001–6004 (1988).
Girard et al., Thromb. Res. 55, 37–50 (1989).
Day et al., Blood 76, 1538–45 (1990).
Pedersen et al., J. Biol. Chem. –265, 16786–16793 (1990).
Haskel et al., Circulation 84, 821–827 (1991).
Diaz–Collier et al., Thromb. Haemost. 71, 339–346 (1994).
Wun et al., Blood 79, 430–438 (1992).
Broze et al., Blood 71, 335–343 (1988).
Broze & Miletich, Proc. Natl. Acad. Sci. –84, 1886–90 (1987).
Rapaport, Blood 73, 359–365 (1989).
Goodman & Gilman, The Pharmaceut. Basis of Therap., Ch. 58, pp. 1348–53, 6th ed. (1980).
The Merck Index, No. 4571, 11th ed. 1989.
Girard et al., Science 248, 1421–1424 (1990).

*Primary Examiner*—Chhaya D. Sayala
*Attorney, Agent, or Firm*—Scott J. Meyer

[57] ABSTRACT

A pre-formed anticoagulant heparin/TFPI complex which consists of a weight ratio of at least 1.25 parts of heparin to one part of TFPI and its use in inhibiting blood cogulation.

17 Claims, 8 Drawing Sheets

PRE-FORMED ANTICOAGULANT HEPARIN/TFPI COMPLEXES

CROSS-REFERENCE TO RELATED APPLICATIONS

This is a continuation-in-part of application Ser. No. 08/453,937, filed May 30, 1995, which is a continuation-in-part of application Ser. No. 08/166,186, filed Dec. 13, 1993, abandoned which in turn is a continuation of application Ser. No. 07/573,083, filed Aug. 27, 1990abandoned.

BACKGROUND OF THE INVENTION

This invention relates to a pre-formed anticoagulant complex of heparin and tissue factor pathway inhibitor (TFPI).

TFPI is a naturally occurring glycoprotein inhibitor of the extrinsic pathway of blood coagulation. The name "tissue factor pathway inhibitor" has been accepted by the International Society on Thrombosis and Hemostasis, Jun. 30, 1991, Amsterdam. TFPI was previously known as lipoprotein-coagulation-associated inhibitor (LACI).

TFPI was first purified from a human hepatoma cell line, Hep G2, as described by Broze and Miletich:

Proc. Natl. Acad. Sci. USA 84, 1886–1890 (1987), and subsequently from human plasma as reported by Novotny et al., J. Biol. Chem. 264, 18832–18837 (1989); and Chang liver and SK hepatoma cells as disclosed by Wun et al., J. Biol. Chem. 265, 16096–16101 (1990).

TFPI cDNA have been isolated from placental and endothelial cDNA libraries as described by Wun et al., J. Biol. Chem. 263, 6001–6004 (1988); and Girard et al., Thromb. Res. 55, 37–50 (1989).

Recombinant TFPI has been expressed as a glycosylated protein using mammalian cell hosts including mouse C1267 cells as disclosed by Day et al., Blood 76, 1538–1545 (1990), baby hamster kidney cells as reported by Pedersen et al., J. Biol. Chem. 265, 16786–16793 (1990), Chinese hamster ovary cells and human SK hepatoma cells as described by Wun et al., Thromb. Haemost. 68, 54–59 (1992).

The C127 TFPI has been used in animal studies and was shown to be effective in the inhibition of tissue factor-induced intravascular coagulation in rabbits according to Day et al., supra, and in the prevention of arterial reocclusion after thrombolysis in dogs as described by Haskel et al., Circulation 84, 821–827 (1991).

Recombinant TFPI also has been expressed as a non-glycosylated protein using E. coli host cells and obtaining a highly active TFPI by in vitro refolding and ion-exchange chromatography as described by Diaz-Collier et al., Thromb. Haemost. 71, 339–346 (1994).

The production and use of TFPI as an inhibitor of blood coagulation is further described in U.S. Pat. Nos. 4,966,852, 5,212,091, 5,276,015, 5,466,783.

Although the synergistic effect upon coagulation when heparin and TFPI are independently added to whole plasma is disclosed by Wun, Blood 79, 430–438 (1992), and in co-pending application Ser. No. 08/453,937, the present application further describes the unexpected anticoagulant activity obtained by the addition of pre-formed heparin/TFPI complexes to plasma.

In order to elucidate the significance of the difference between addition of these pre-formed complexes vs. the independent addition of heparin and TFPI to plasma, the following further background information is provided:

Coagulation is initiated when damage to blood vessels at the site of a wound allows the exposure of blood to tissue factor (TF) present constitutively on cells beneath the endothelium. The factor VII or VIIa present in plasma then binds to TF, and the factor VIIa-TF complex activates limited quantities of factor X and factor IX.

This initial factor Xa/IXa generation provides sufficient thrombin to activate platelets, factor V and factor VIII. With the generation of factor Xa, however, further cascade is dampened by the inhibitory effect of tissue factor pathway inhibitor (TFPI) which forms an inhibitory complex with factor Xa and factor VIIa-TF. Additional factor Xa and thrombin are then produced and amplified through the alternative pathway involving factor IXa and VIIIa.

The above sequence of events are key features of the current revised theory of the coagulation cascade [Broze, Annu. Rev. Med. 46: 103–112 (1995); Roberts and Tabares, Molecular Basis of Thrombosis and Hemostasis, (High, K. A. and Roberts, H. R. eds.), Marcel Dekker, pp. 35–50, 1995]. According to this theory, the classical extrinsic and intrinsic pathways are both involved in the TF-induced coagulation reactions.

The TFPI molecule contains a highly negatively charged N-terminus, three tandem Kunitz-type inhibitory domains (K1, K2, and K3), and a highly positively charged carboxyl terminus [(Wun, et al., J. Biol. Chem. 263:6001–6004, (1988)]. It inhibits factor Xa via the K2 domain and the factor VIIa-TF complex via the K1 domain, and thus blocks the initial steps of the extrinsic pathway. The K3 domain and the carboxyl terminal peptide contain consensus sequences for binding to glycosaminoglycans and are responsible for binding to heparin [Enjyoji, et al., Biochemistry 34:5725–5735 (1995)].

The carboxyl terminal peptide of TFPI is essential for maximum expression of its anticoagulant activity in a dilute tissue factor-based coagulation assay [Nordfang, et al., Biochemistry 30:10371–10376 (1991); Wesselschmidt, et al., Blood 79:2004–2010 (1992); Wun, et al., Thromb. Haemost. 68:54–59 (1992)].

Heparin has been widely used as an anticoagulant in clinical conditions. Its anticoagulant effect is due to its catalytic action on the inhibition of thrombin and other proteases of the intrinsic and common pathways by antithrombin III [Casu, Adv. Carbohydr. Chem. Biochem. 43:51–134 (1985)].

In a one-stage TF-induced coagulation assay, it was shown that TFPI and heparin can exert synergistic anticoagulant effects in whole plasma [Wun, Blood 79:430–438 (1992)]. The mechanism of heparin/TFPI synergy in plasma has not been elucidated. In a purified system, heparin enhances the rate of factor Xa inhibition by TFPI in a concentration dependent and biphasic manner, suggesting that acceleration of inhibition occurs at least in part through a "template" mechanism [Wesselschmidt, et al., Blood Coag. Fibrinol. 4: 661–669 (1993)].

However, this template mechanism cannot fully account for the heparin/TFPI synergy in the whole plasma system, since synergy does not occur in antithrombin III-deficient plasma indicating its dependence on the anticoagulant activity of antithrombin III/heparin [Nordfang, et al., Thromb. Haemost. 70: 448–453 (1993)]. Thus, the heparin/TFPI synergy phenomenon in plasma may arise from other mechanisms. As described herein below, one possible mechanism is that TFPI and heparin provide efficient inhibition of the extrinsic and intrinsic pathways, respectively, and together, they give rise to tighter regulation of the entire coagulation cascade.

BRIEF DESCRIPTION OF THE INVENTION

In accordance with the present invention, pre-formed heparin/TFPI complexes are provided as useful anticoagulants of blood plasma. Unexpectedly, it was found that the anticoagulant activity of the pre-formed complexes exhibited either lower or higher activities than expected from the sum of the effects of heparin and TFPI alone, depending upon the weight ratio of the two components. It was also found that the pharmacokinetics of the heparin/TFPI complexes was very different from that of TFPI, and the complexes surprisingly showed slower clearance than TFPI.

It is critical to the invention, that in order to provide higher anticoagulant activity, a weight ratio of at least 1.25 parts of heparin to one part of TFPI is required in the heparin/TFPI complexes. When a pre-formed heparin/TFPI complex at a weight ratio below 1.25:1 was added to plasma, the tissue-factor induced clotting time was shorter than when TFPI was added alone (without addition of heparin). A preferred range of the weight ratio of the active complex is from 1.25 to about 100 parts of heparin to one part of TFPI.

The pre-formed heparin/TFPI complex thus provides for a reduction in the dose requirement of TFPI for inhibition of coagulation. In the case of full length (FL-) TFPI, the complex with heparin also improves the solubility of the FL-TFPI.

Another particular advantage of the heparin/TFPI complexes of the invention is seen from its beneficial inhibitory effect in a glomerulonephritis model in which a significant reduction of glomerular fibrin deposition, proteinuria and renal impairment is obtained which was not obtained by separate administration of either heparin or TFPI.

The pre-formed heparin/TFPI complexes can be conveniently prepared by simple admixture of the heparin and TFPI in the above-stated weight ratio in physiologically acceptable buffer solution, e.g. normal physiologic saline (0.15M NaCl, pH 7.4). Preferably, the TFPI is dissolved in a buffer that permits high solubility of ≧5 mg/ml, e.g., (A) 2M urea-saline, or (B) 0.2M L-arginine-20 mM phosphate-saline, or (C) 5% mannitol-0.1 mM HCl, and the heparin is dissolved in saline. The respective TFPI and heparin solutions are then mixed to form soluble heparin/TFPI complexes and the mixture diluted in saline solution.

The heparin preferably is unfractionated heparin and preferably consists of about 160 to about 175 USP Units of heparin per mg.

Although complexes of heparin with carboxy-truncated (CT-) TFPI also exhibit synergistic anticoagulant action as shown herein, complexes with full-length (FL-) TFPI are preferred.

DETAILED DESCRIPTION OF THE INVENTION

While the specification concludes with claims particularly pointing out and distinctly claiming the subject matter regarded as forming the present invention, it is believed that the invention will be better understood from the following description of preferred embodiments of the invention taken in conjunction with the accompanying drawings which are graphical representations in which:

BRIEF DESCRIPTION OF THE DRAWINGS

FIG. 1, in two parts, A and B, shows: Effects of heparin and FL-TFPI on PT and APTT.

Measurement of PT and APTT are as described in METHODS. PT and APTT ratios are calculated by dividing the clotting times in the presence of the indicated amounts of FL-TFPI or heparin by the clotting times in the absence of anticoagulants.

FIG. 2, in two parts, A and B, shows: Effects of TFPI or heparin and their combination on dPT.

dPT assay was carried out using 1:4 dilution of Simplastin®. Closed square and closed triangle on the abscissa indicate the clotting times of the plasma supplemented with control buffer and 2 μg/ml FL-TFPI, respectively.

(□) Plasma supplemented with indicated concentrations of heparin.

(Δ) Plasma supplemented with indicated concentration of heparin followed by addition of 2 μg/ml of FL-TFPI.

(▲) Plasma supplemented with preformed heparin/FL-TFPI complexes such that the heparin concentrations are as indicated and FL-TFPI concentration is 2 μg/ml.

dPT assay was carried out using 1:40 dilution of Simplastin®. Closed square and closed triangle on the abscissa indicate the clotting times of the plasma supplemented with control buffer and 0.3 μg/ml FL-TFPI, respectively.

(□) Plasma supplemented with indicated concentrations of heparin.

(Δ) Plasma supplemented with indicated concentration of heparin followed by addition of 0.3 μg/ml of FL-TFPI.

(▲) Plasma supplemented with preformed heparin/FL-TFPI complexes such that the heparin concentrations are as indicated and FL-TFPI concentration is 0.3 μg/ml.

dPT assay was carried out using 1:4 dilution of Simplastin®. Closed square and closed triangle on the abscissa indicate the clotting times of the plasma supplemented with control buffer and 2 μg/ml FL-TFPI, respectively.

(□) Plasma supplemented with indicated concentrations of N-acetyl heparin.

(Δ) Plasma supplemented with indicated concentration of N-acetyl heparin followed by addition of 2 μg/ml of FL-TFPI.

(▲) Plasma supplemented with preformed N-acetyl heparin/FL-TFPI complexes such that the N-acetyl heparin concentrations are as indicated and FL-TFPI concentration is 2 μg/ml.

dPT assay was carried out using 1:4 dilution of Simplastin®. Closed square and closed triangle on the abscissa indicate the clotting times of the plasma supplemented with control buffer and 2 μg/ml FL-TFPI, respectively.

(□) Plasma supplemented with indicated concentrations of LMWH.

(Δ) Plasma supplemented with indicated concentration of LMWH followed by addition of 2 μg/ml of FL-TFPI.

(▲) Plasma supplemented with preformed LMWH/FL-TFPI complexes such that the LMWH concentrations are as indicated and FL-TFPI concentration is 2 μg/ml.

(○) Plasma level of TFPI measured by PCFIA assay following bolus injection of FL-TFPI.

(□) Plasma level of TFPI measured by dPT functional assay following bolus injection of FL-TFPI.

(Δ) Plasma level of TFPI measured by PCFIA assay following bolus injection of heparin/FL-TFPI complex. (N=3 each).

For heparin/FL-TFPI, a bolus of preformed heparin (0.24 mg/kg)/FL-TFPI (0.19 mg/kg) complex was injected followed by constant infusion of heparin (5.4 μg/kg/min)/FL-TFPI (4.3 μg/kg/min) complex. Infusions were carried out over a 4-h period. Plasma levels of TFPI were measured by PCFIA assay.

In order to illustrate the invention in greater detail, the following exemplary laboratory preparative work and detailed Examples were carried out. It will be appreciated, however, that the invention is not limited to these specific Examples which are provided for purposes of illustration and not limitation.

EXAMPLES

MATERIALS.

Rabbit brain thromboplastin (Simplastin®, Tissue factor TF) was obtained from Organon Teknika (Durham, N.C.).

Dade's activated cephaloplastin reagent was supplied by American Scientific Produce (McGraw Park, Ill.).

Unfractionated heparin (UHF) and low molecular weight heparin (LMWH) (Lovenox®) were purchased from Elkin-Sinn (Cherry Hill, N.J.) and Rhone-Poulenc Rorer (Collegeville, Pa.), respectively.

N-acetyl heparin, fluoro-isothiocyanate isomer I(FITC), 1-ethyl-3-(3-dimethylaminopropyl) carbodiimide (EDAC) were supplied by Sigma (St. Louis, Mo.).

Human plasma was provided by The American Red Cross (St. Louis, Mo.).

Pooled plasma was prepared by mixing four (4) units of individual plasmas, and TFPI-depleted pooled plasma was obtained by passing the pooled plasma through a rabbit anti-human TFPI-Ig Sepharose® 4B column as described previously [(Wun, *J. Biol. Chem.* 265:16096–16101 (1990)].

Recombinant full-length (FL-) TFPI and carboxy terminus truncated (CT-)TFPI were isolated as described by Wun, et al., *Thromb. Haemost.* 68: 54–59 (1992).

The hybridoma cell line 2H8 producing a monoclonal antibody against TFPI was a gift from Dr. George Broze, Jr., Washington University.

2H8 monoclonal antibody was purified from the mouse ascites by affinity chromatography on a protein A-Sepharose® 4B column.

Fluoricon®-CA assay plate and carboxyl-polystyrene particle (0.7–0.9 μ) were obtained from Idexx (Westbrook, Me.).

PROTHROMBIN TIME (PT) ASSAY.

Ninety (90) μl of plasma were mixed with 10 μl of DB (dilution buffer containing 10 mM Tris/HCl, pH 7.4, 150 mM NaCl, 1 mM Na$_2$SO$_4$, 1 mg/ml bovine serum albumin, and 0.02% NaN$_3$), FL-TFPI solution, or heparin solution in the Fibrometer well at 37° for 1 min. Two hundred (200) μl of Simplastin® were then added and the time to clotting was recorded.

ACTIVATED PARTIAL THROMBOPLASTIN TIME (APTT) ASSAY.

Ninety (90) μl of plasma were mixed with 10 μl of DB, FL-TFPI solution, or heparin solution in the Fibrometer well at 37° for 1 min. One hundred (100) μl of Dade's activated cephaloplastin reagent were added and the mixture was incubated for exactly 2 min. A calcium solution (100 μl of 25 mM CaCl$_2$) was added and the time to clotting was recorded.

DILUTE PROTHROMBIN TIME (dPT) ASSAY.

Rabbit brain thromboplastin (TF;Simplastin®) was diluted to varying degrees ranging from 1:4 to 1:50 with a buffer containing 12.5 mM CaCl$_2$, 75 mM NaCl, 0.5 mg/ml bovine serum albumin, and 0.02% NaN$_3$, for determination of TF-induced clotting time in human plasma. Fifty (50) μl of human plasma were mixed with 50 μl of DB, heparin, TFPI, or preformed complexes of heparin/TFPI in DB in the well of a Fibrometer at 37° for 1 min. Two hundred (200) μl of appropriately diluted thromboplastin reagent were then added and the time to clotting was determined.

The dPTs reported here are the average of 2 to 8 determinations, depending on the length of the clotting time. When the clotting time was short (<100 sec), the variations between determinations are small and 2–4 assay values were averaged for each data point. When the clotting time is long (>100 sec), the variations between determinations are larger and 5–8 assay values are averaged for each data point. The assays were observed for up to 1000 sec. The concentrations of heparin and TFPI are expressed as units or μg per ml of plasma, not as that in the final assay mixture.

PARTICLE CONCENTRATION FLUORESCENCE IMMUNOASSAY (PCFIA) of TFPI.

Carboxyl-polystyrene beads were coated with 2H8 monoclonal antibody points over a 6-hr period. Plasma was separated by centrifugation and stored at −70° until PCFIA assay.

For constant infusion studies, a bolus of FL-TFPI (0.5 mg/kg) or pre-formed heparin (0.24 mg/kg)/FL-TFPI (0.19 mg/kg) complex was injected through the femoral vein, followed by constant infusion of FL-TFPI (11.4 μg/kg/min) or heparin (5.4 μg/kg/min)/FL-TFPI (4.3 μg/kg/min) complex over a 4-hr period. Blood collection and plasma sample preparation were carried out as described above.

Plasma levels of TFPI antigen were measured by PCFIA assay. Functional TFPI activity in the plasma was also measured by dPT assay using each rabbit's own control plasma supplemented with known concentrations of FL-TFPI as a reference standard [Palmier, et al., *Thromb. Haemost.* 68, 33–36 (1992)]. Data from individual animals were fitted to the general bi-exponential equation:

$$C = Ae^{-at} + Be^{-bt}$$

where C is the concentration of TFPI at time t, and A and B are the intercept values ($t_o$) extrapolated from a and b, the first order elimination rate constants.

RESULTS
Effects of heparin and FL-TFPI on PT and APTT.

Figure 1A:
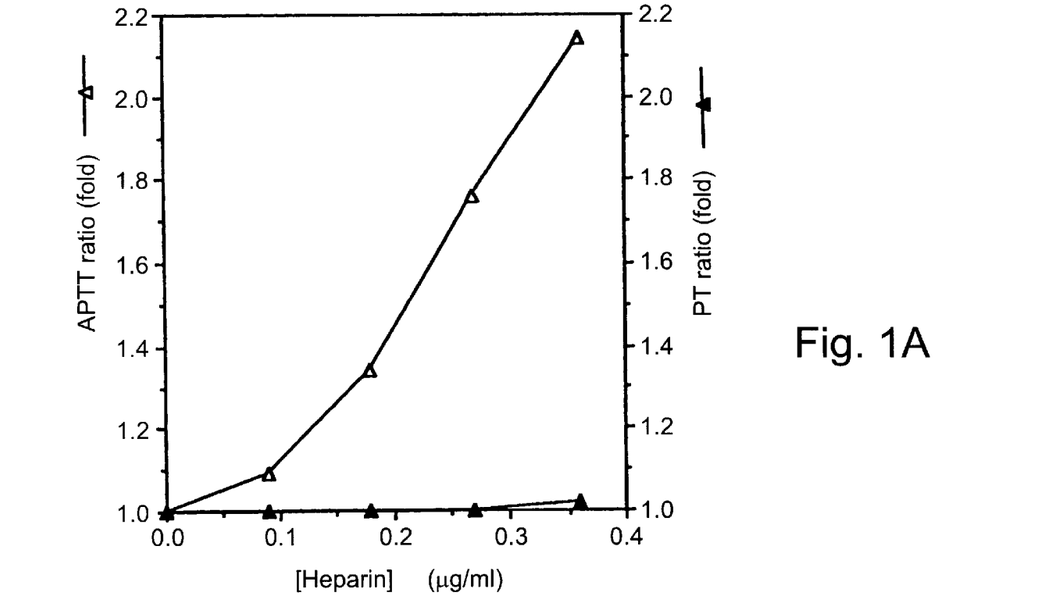
FIG. 1A: Effect of heparin on PT and APTT.

PT is a global test that primarily measures the functionality of the extrinsic and the common pathways; while APTT is a procedure which evaluates that of the intrinsic and the common pathways. The individual effects of heparin and FL-TFPI on PT and APTT were examined to determine the primary sites of their actions. As shown in FIG. 1A, FL-TFPI caused a much greater increase of the PT ratio than the APTT ratio (PT and APTT ratios are defined as the clotting time in the presence of added anticoagulant over that in the absence of added anticoagulant).

Figure 1B:
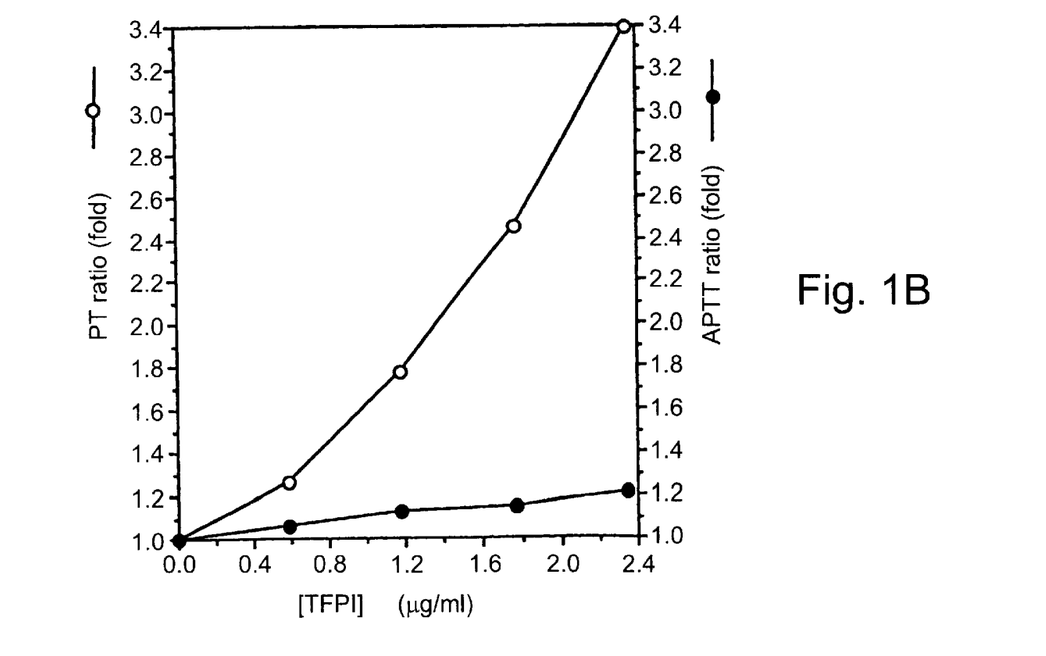
FIG. 1B: Effect of FL-TFPI on PT and APTT.

In contrast, heparin effected a much greater increase of APTT ratio than PT ratio (FIG. 1B). These results indicate that FL-TFPI primarily affects the extrinsic pathway and heparin mainly inhibits the intrinsic pathway.
Synergistic anticoagulant action as a result of sequential addition of heparin and TFPI to TFPI-depleted plasma.

In applicant's previously reported work, it was demonstrated that addition of increasing concentrations of heparin and recombinant C127 cell derived-TFPI to TFPI-depleted plasma (without premixing heparin with TFPI), resulted in progressively greater prolongation of clotting time than would be expected from mere additive effects of heparin alone and TFPI alone [Wun, Blood 79, 430–438 (1992)].

However, a roughly 50:50 mixture of FL-TFPI and CT-TFPI was used in that study because of unavailability of homogeneous preparations of each component at that time. Thus, it was not established whether synergy is a result of the combination of FL-TFPI/heparin, CT-TFPI/heparin, or both.

Figure 2A:
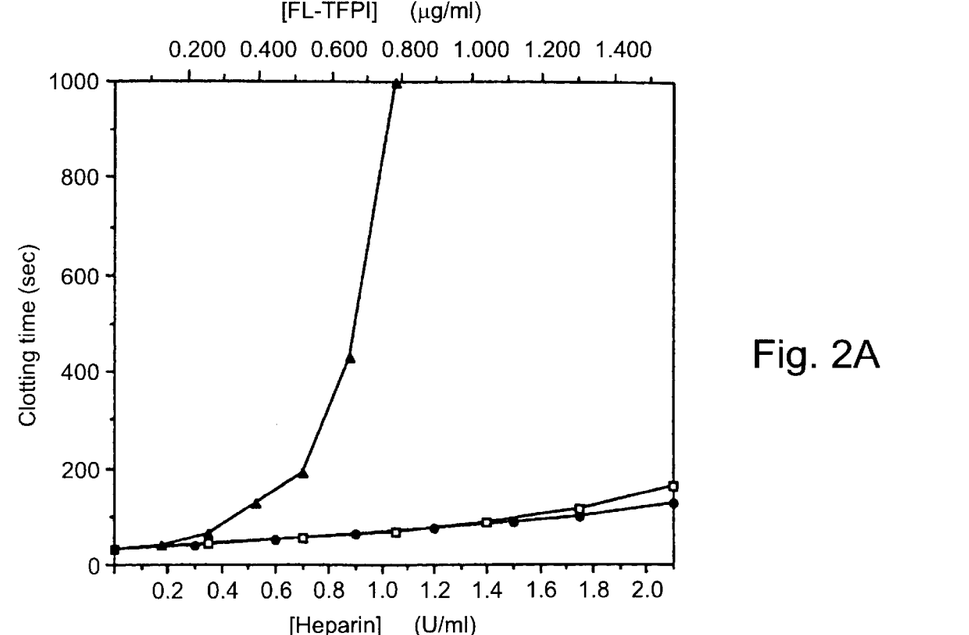
FIG. 2A: Effects of FL-TFPI (□), heparin (●), and sequential addition of FL-TFPI and heparin (▲) on clotting time.
Figure 2B:
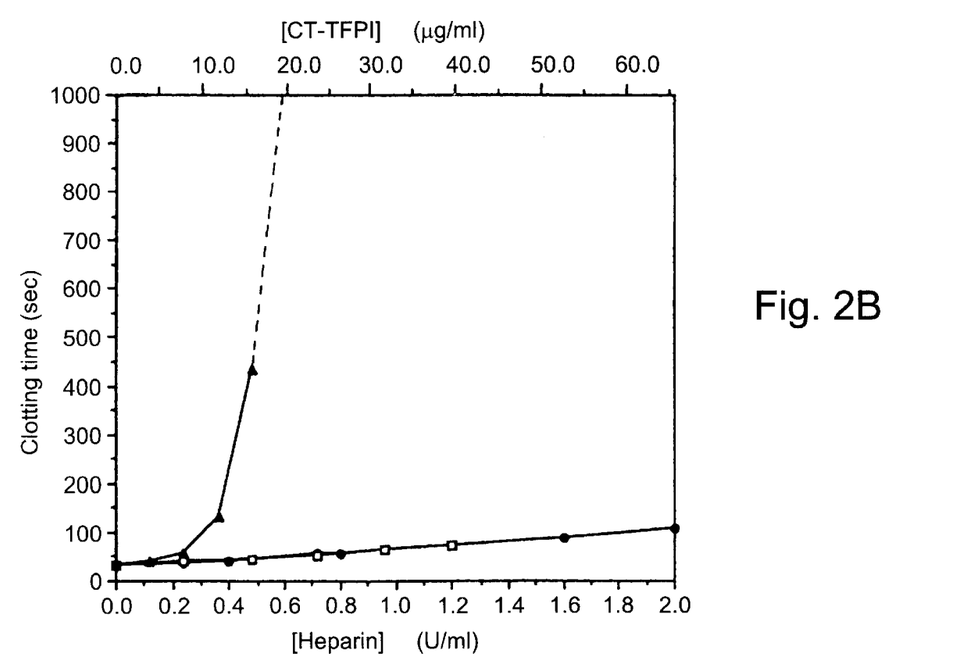
FIG. 2B: Effects of CT-TFPI (□), heparin (●), and sequential addition of CT-TFPI and heparin (▲) on clotting time. dPTs were determined as described in METHODS using 1:50 dilution of Simplastin®.

In the present work, FL-TFPI and CT-TFPI were separated by Mono S chromatography as described before [Wun, et al., Thromb. Haemost. 68, 54–59 (1992)], and the effects of heparin, FL-TFPI, or CT-TFPI alone, and combinations of heparin/FL-TFPI, and heparin/CT-TFPI were compared. FIGS. 2A and B show the results. Note that:

(1) The concentration of CT-TFPI alone required for doubling the clotting time is ~37 fold that required by FL-TFPI alone, suggesting that FL-TFPI is much more potent in prolonging the clotting time than CT-TFPI;

(2) Increasing concentrations of heparin, FL-TFPI, and CT-TFPI alone increasingly prolong the clotting time in a moderate manner; and (3) Sequential addition of heparin and FL-TFPI (FIG. 1A), or heparin and CT-TFPI (FIG. 1B) give rise to greater prolongation of clotting time than expected from the additive effects of the individual components, indicating synergistic anticoagulant actions of both combinations.

Solubility of FL-TFPI and heparin/FL-TFPI complexes.

As FL-TFPI is far more potent than CT-TFPI in prolonging the TF-induced clotting time, the former was chosen for further tests. Glycosylated, recombinant mammalian cell derived-FL-TFPI [Wun, et al., Thromb. Haemost. 68, 54–59, (1992)] has a very poor solubility in normal saline. Inclusion of 10–20 mM phosphate or sulfate in the saline solution improved the solubility to several mg/ml. The solubility of non-glycosylated recombinant E. coli-derived FL-TFPI [Diaz-Collier, et al., Thromb. Haemost. 71, 339–346, (1994)] in saline solutions is even lower. Its solubility in Dulbecco's phosphate-buffered saline is estimated to be approximately 200 µg/ml. In 0.15M of phosphate, pH 7.4, the solubility of FL-TFPI exceeds 5 mg/ml, suggesting that high concentrations of divalent anions may help solubilize FL-TFPI.

FL-TFPI binds strongly to heparin with 0.6–1M NaCl required for effective dissociation [Pederson, et al., Blood 79, 2004–2010 (1992)]. For solubility and potential synergy considerations, we therefore explored the formation of heparin/FL-TFPI complexes at different weight ratios.

In an initial test, FL-TFPI was mixed with varying amounts of heparin such that the concentration of FL-TFPI was maintained constant at 4.5 mg/ml and the heparin/FL-TFPI weight ratios were 1:1, 1:2, 1:4, 1:8 and 1:16. After dialysis of the solutions against Dulbecco's phosphate buffered saline, the solution with a 1:16 heparin/FL-TFPI ratio became cloudy with precipitate, while all the other solutions remained clear.

Absorbance measurements at 280 nm confirmed that all the clear solutions contained the original concentration of FL-TFPI. Thus, heparin/FL-TFPI complexes formed have solubilities ≥4.5 mg/ml in phosphate buffer saline as long as the weight ratio of heparin to FL-TFPI is larger than 1:8.
Sequential addition of heparin and TFPI vs. addition of preformed heparin/TFPI complexes to the plasma: Comparison of their effects on TF-induced clotting.

Figure 3:
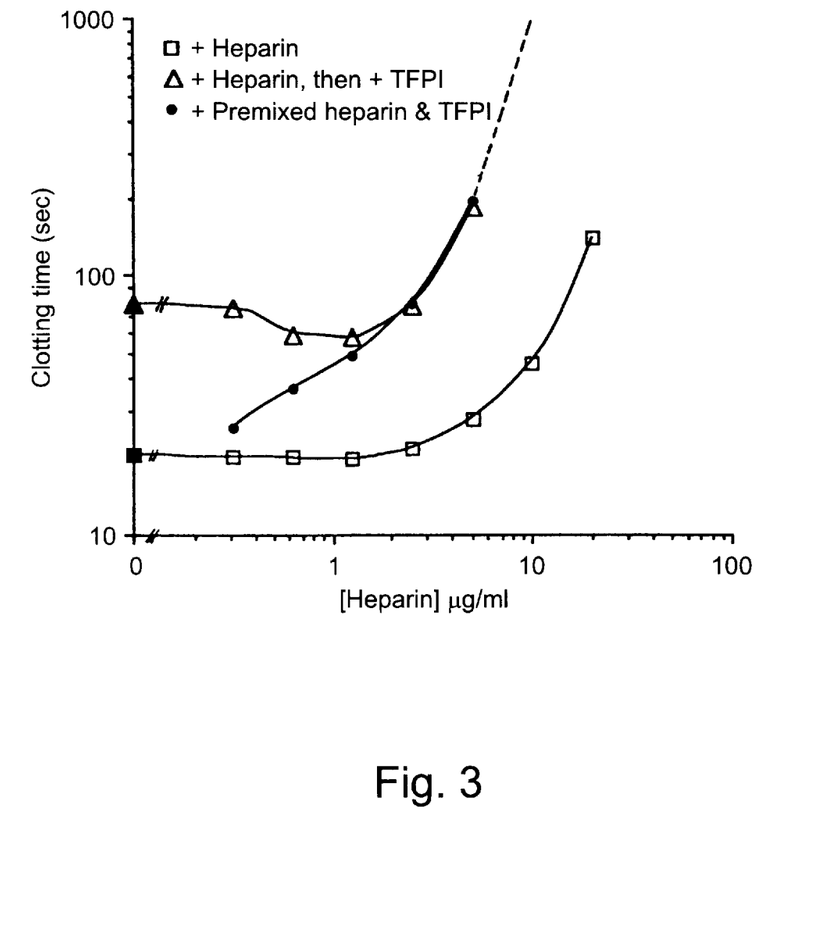
FIG. 3 shows: Effects of sequential addition of heparin and FL-TFPI vs. addition of preformed heparin/FL-TFPI complexes to plasma on TF-induced clotting.

In one-stage TF-induced plasma clotting assay, clotting time is dependent on the concentration of TF and the concentrations of anticoagulants present. FIG. 3 shows the effects of heparin, FL-TFPI, and their combination on coagulation time when plasma was induced to clot by addition of 1:4 dilution of Simplastin®. In the absence of added anticoagulants, the addition of this concentration of TF caused the plasma to clot in 20 sec (closed square).

Addition of heparin up to 1.25 µg/ml did not alter the clotting time. The clotting time was progressively prolonged as the heparin increased beyond this concentration (□).

Addition of 2 µg/ml of FL-TFPI alone prolonged the clotting time to 78 sec (closed triangle).

Addition of up to 1.25 µg/ml of heparin followed by addition of 2 µg/ml of FL-TFPI (Δ) caused a slight shortening of clotting time (e.g. at 1.25 µg/ml heparin +2 µg/ml FL-TFPI, the clotting time shortened to 58 sec).

Addition of 2.5 µg/ml of heparin followed by addition of 2 µg/ml FL-TFPI (Δ) progressively showed synergistic anticoagulation effects (e.g. 10 µg/ml of heparin alone and 2 µg/ml of FL-TFPI alone prolong the clotting time 26 sec and 58 sec, respectively; while sequential addition of both resulted in much greater degree of anticoagulation such that the plasma does not clot for more than 1000 sec).

Surprisingly, when heparin FL-TFPI complexes at weight ratios <1.25:1 were pre-formed before addition to the plasma (●), the clotting times were shorter than adding FL-TFPI alone or sequential addition of heparin and FL-TFPI, for example:

addition of control buffer without anticoagulants gave a clotting time of 20 sec;

addition of 2 µg/ml of FL-TFPI alone gave a clotting time of 78 sec;

addition of 0.31 µg/ml of heparin followed by addition of 2 µg/ml of FL-TFPI gave a clotting time of 75 sec; and addition of a premixed complex consisting of 0.31 µg/ml heparin and 2 µg/ml of FL-TFPI gave a clotting time of 23 sec.

However, when heparin/FL-TFPI complexes were formed at ratios ≧1.25:1, the clotting times were not different from sequential addition of heparin and FL-TFPI and synergism was observed (●). Thus, to preserve the anticoagulant activity of FL-TFPI or to achieve synergy by using the preformed heparin/FL-TFPI complex, heparin/FL-TFPI weight ratios of ≧1.25:1 are required under these conditions.

The amount of TF present in patho-physiological states is not known in most cases. In order to establish the optimum weight ratios of pre-formed heparin/FL-TFPI complexes that possess maximum or enhanced activity, a test was carried out at a 1:40 dilution (1/10th of above test) of Simplastin®.

Figure 4:
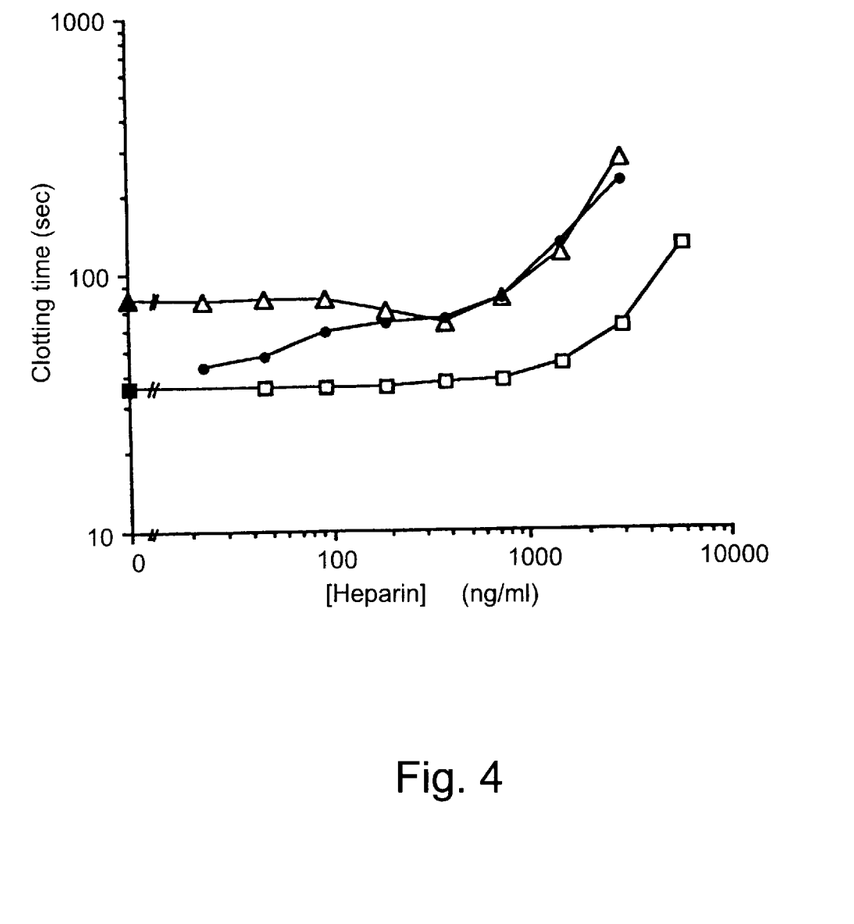
FIG. 4 shows: Effects of sequential addition of heparin and FL-TFPI vs. addition of preformed heparin/FL-TFPI complexes to plasma on TF-induced clotting.

FIG. 4 shows that very similar results to that of FIG. 3 were obtained. Notably, depressed activity was seen when the preformed heparin/FL-TFPI complex was present at <0.375 µg/ml of heparin and 0.3 µg/ml of FL-TFPI (heparin/FL-TFPI weight ratios <1.25:1), and the activity was preserved or enhanced when the ratios were ≧1.25:1. Thus, despite a 10-fold variation of TF, the optimum ratios of heparin/FL-TFPI complexes to achieve maximum activity remained the same.

Sequential addition of N-acetyl heparin and TFPI vs. addition of preformed N-acetyl heparin/TFPI complexes.

N-acetyl heparin is a modified form of heparin that possesses very little anticoagulant activity. In a dPT assay using a 1:4 dilution of Simplastin®, up to 40 µg/ml of N-acetyl heparin did not alter the clotting time (FIG. 5, closed and open squares, clotting times ~18 sec).

Figure 5:
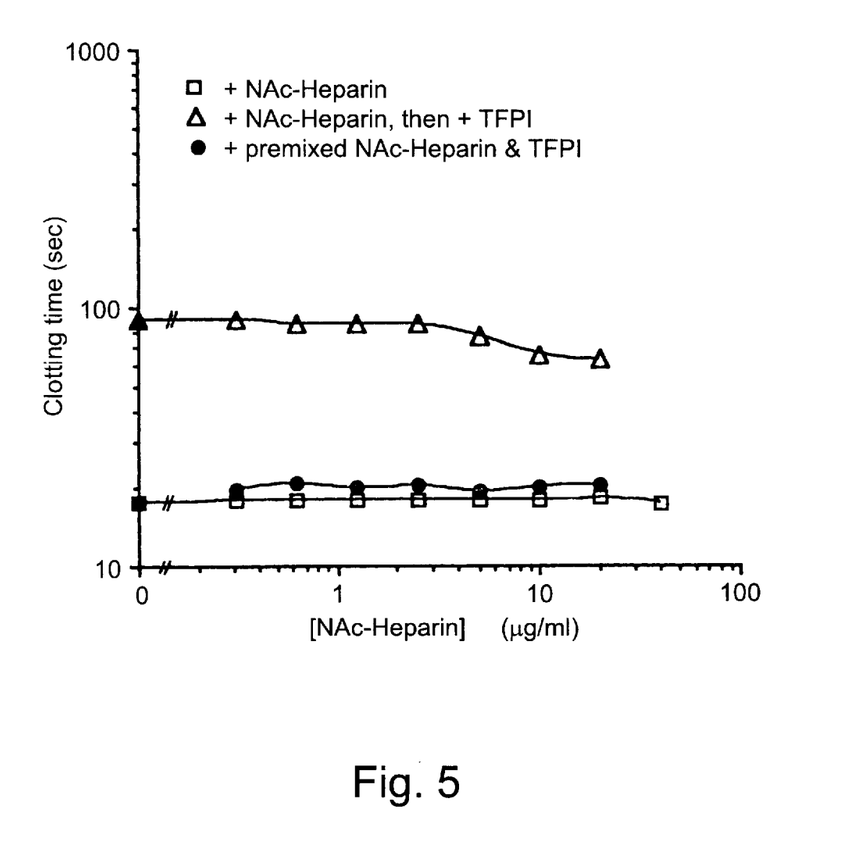
FIG. 5 shows: Effects of sequential addition of N-acetyl heparin and FL-TFPI vs addition of preformed N-acetyl heparin/FL-TFPI complexes to plasma on TF-induced clotting.

Addition of 2 µg/ml of FL-TFPI alone caused the plasma to clot at 90 sec (closed triangle).

Addition of increasing concentrations of N-acetyl heparin followed by addition of 2 µg/ml of FL-TFPI (Δ) slightly shortened the clotting time compared to addition of FL-TFPI alone (e.g. the clotting time was 63 sec when 20 µg/ml of N-acetyl heparin and 2 µg/ml of FL-TFPI were sequentially added to the plasma).

When 0.313–20 µg/ml of N-acetyl heparin were premixed with 2 µg/ml of FL-TFPI and the mixtures were added to plasma, the clotting times were all ~20 sec. Thus, sequential addition of N-acetyl heparin and FL-TFPI lead to slight shortening of clotting time as compared to addition of FL-TFPI alone; and pre-formation of N-acetyl heparin/FL-TFPI complexes inhibited the anticoagulant activity of FL-TFPI to a great extent.

Sequential addition of LMWH and TFPI vs. addition of preformed LMWH/TFPI complexes.

LMWH possessed weaker anticoagulant activity on a per weight basis in the dPT assay (FIG. 6) as compared to unfractionated heparin (FIG. 3).

Figure 6:
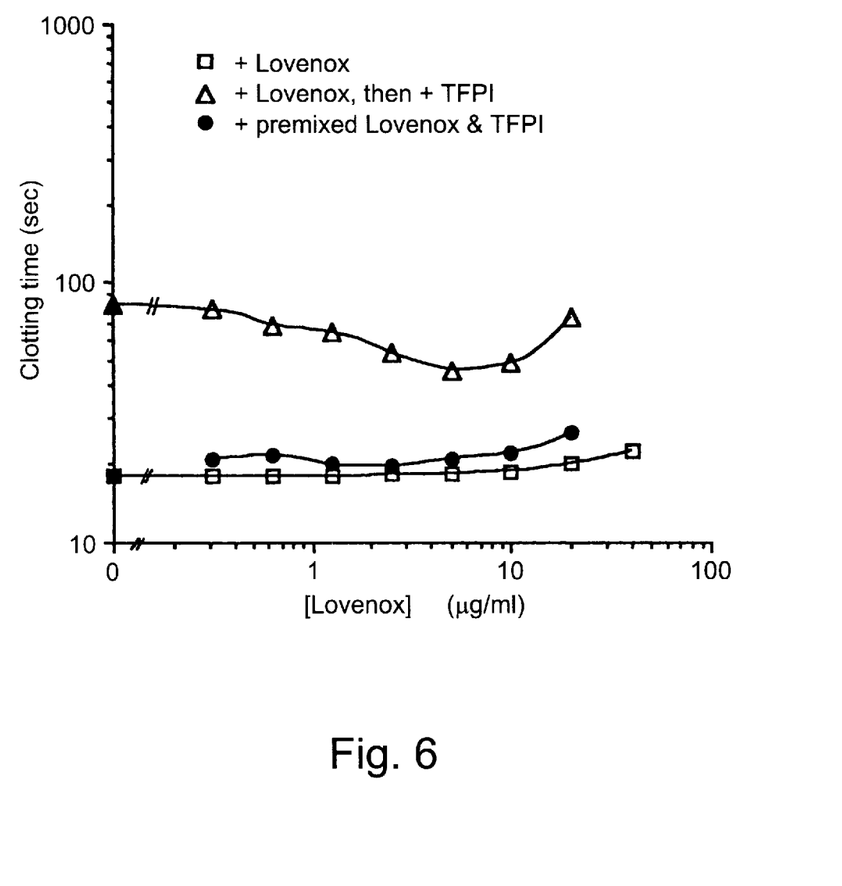
FIG. 6 shows: Effects of sequential addition of LMWH and FL-TFPI vs. addition of preformed LMWH/FL-TFPI complexes to plasma on TF-induced clotting.
Figure 7:
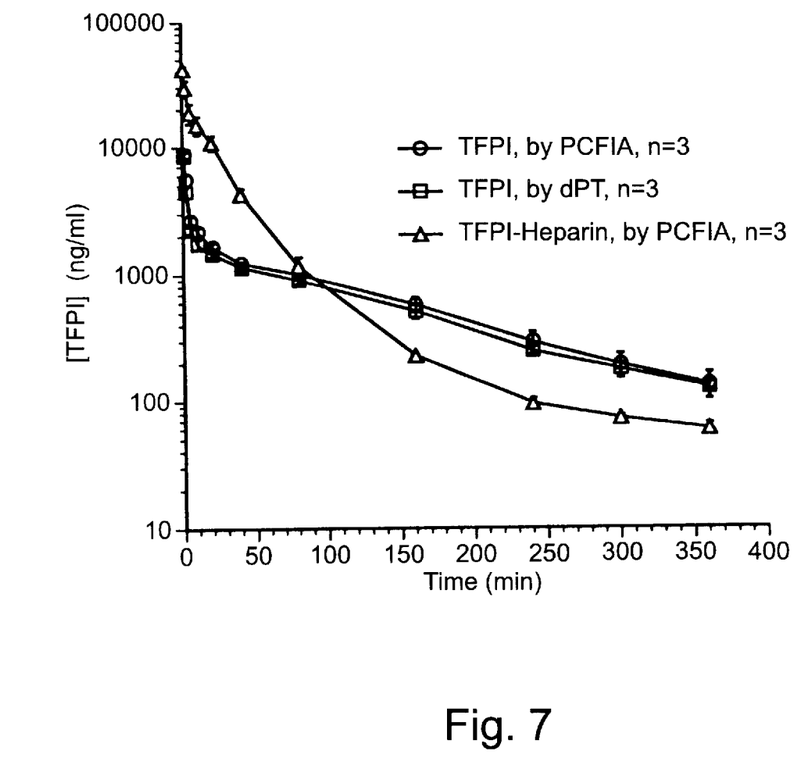
FIG. 7 shows: Pharmacokinetics of FL-TFPI following bolus injection of FL-TFPI or heparin/FL-TFPI complex. The pharmacokinetic study was carried out as described in METHODS. Rabbits were injected with a bolus of FL-TFPI (1.5 mg/kg) or heparin (1.9 mg/kg)/FL-TFPI (1.5 mg/kg) complex.

In a dPT assay using 1:4 dilution of Simplastin®, up to 5 µg/ml of LMWH did not alter the clotting times (FIG. 6, closed and open square, clotting times ~18 sec).

Addition of 10, 20, and 40 µg/ml of LMWH increase the clotting time to only 19, 20 and 22 sec., respectively.

Addition of 2 µg/ml of FL-TFPI alone caused the plasma to clot at 82 sec. (closed triangle).

Addition of up to 10 µg/ml of LMWH followed by addition of 2 µg/ml of FL-TFPI (●) moderately shortened the clotting time as compared to the addition of FL-TFPI alone (e.g. the clotting time was 46 sec when 5 µg/ml of LMWH and 2 µg/ml of FL-TFPI were sequentially added to the plasma).

Addition of 20 µg/ml of LMWH followed by addition of 2 µg/ml of FL-TFPI gave a clotting time of 75 sec. which was close to that of adding FL-TFPI alone (82 sec.).

When 0.313–20 µg/ml of LMWH were premixed with 2 µg/ml of FL-TFPI and the mixtures were added to plasma, the clotting times (20–26 sec) were much shorter than adding FL-TFPI alone. Thus, unlike unfractionated heparin, pre-formation of LMWH/FL-TFPI complexes in the ratios studied inhibited the anticoagulant activity of FL-TFPI to a large extent.

Pharmacokinetics of FL-TFPI vs. heparin/FL-TFPI complex in rabbits.

Following a bolus injection of FL-TFPI, the pharmacokinetics of the clearance of TFPI antigen as measured by PCFIA assay closely matched the clearance of functional TFPI activity as measured by dPT assay (FIG. 6, ○ and □). Thus, the PCFIA assay faithfully reflected the clearance of FL-TFPI, and the values from this assay were used for calculation of pharmacokinetic parameters. The pharmacokinetics of FL-TFPI was characterized by an initial rapid rate ($t_{1/2}\alpha$=1.4 min) followed by a terminal slower rate ($t_{1/2}\beta$=92 min). In contrast, bolus injection of preformed heparin/FL-TFPI complex had dramatically altered pharmacokinetics with a much slower initial rate of clearance ($t_{1/2}\alpha$=15 min).

The data from individual rabbits can be fitted to a bi-exponential model by non-linear analysis. Pharmacokinetic parameters based on this analysis are listed in Table 1, below. The volume of distributions, $V_d$, for FL-TFPI and heparin/FL-TFPI were 117 and 52 ml, respectively.

The AUC was 274 µg ml$^{-1}$min$^{-1}$ for FL-TFPI and 704 µg ml$^{-1}$min$^{-1}$ for FL-TFPI. The $AUC_\beta$ was dominant for FL-TFPI (92%), and the $AUC_\alpha$ was dominant for heparin/FL-TFPI (88%). The overall clearance was 5.7 ml kg$^{-1}$ min$^{-1}$ for FL-TFPI and 2.2 ml kg$^{-1}$ min$^{-1}$ for heparin/FL-TFPI, a 2.6 fold slower clearance for the latter.

Figure 8:
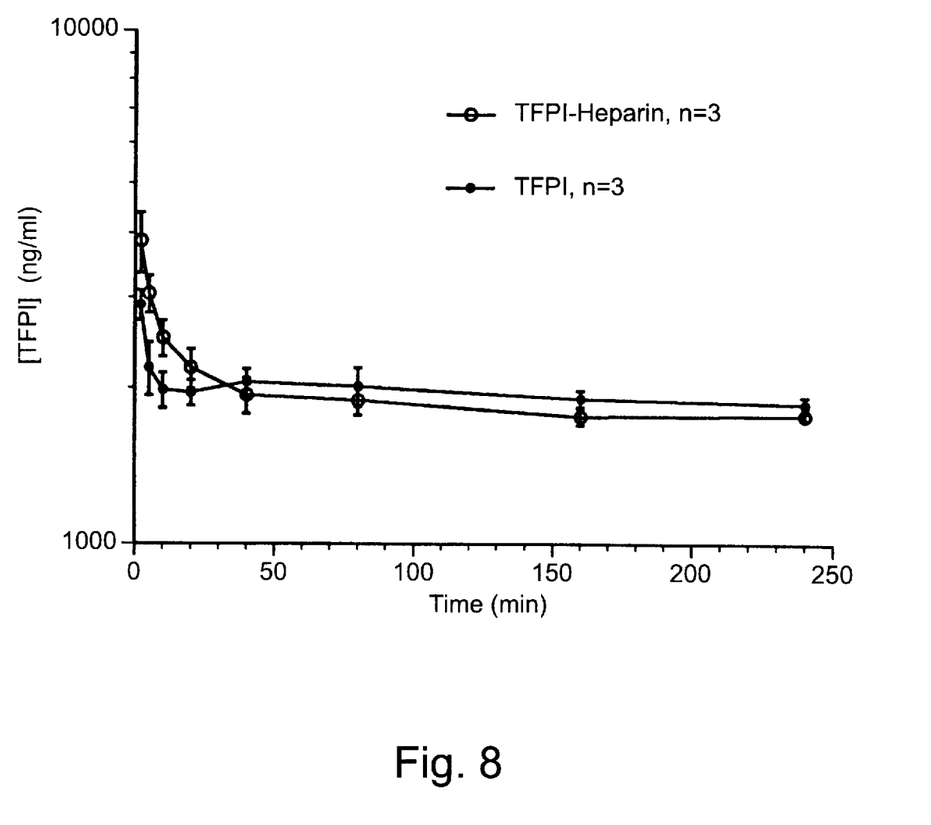
FIG. 8 shows: Plasma levels of TFPI following bolus injection and constant infusion of FL-TFPI or heparin/FL-TFPI complex. For FL-TFPI, a bolus of 0.5 mg/kg was injected through the femoral vein followed by constant infusion of FL-TFPI (11.4 μg/kg/min).

Based on the clearance data, it is believed that the same steady state plasma level of FL-TFPI can be achieved by infusion of a 2.6 fold lower dose in the form of heparin/FL-TFPI complex than by infusion of FL-TFPI. FIG. 8 shows that a steady state plasma level of ~2 µg/ml TFPI was indeed obtained by infusion of either 11.4 µg/kg/min of FL-TFPI or heparin (5.4 µg/kg/min/FL-TFPI (4.3 µg/kg/min) complex.

In applicant's previously reported work, heparin and TFPI that contained both full-length and carboxyl-truncated forms of molecules were shown to exert synergistic anticoagulant effects in a TF-induced clotting assay when they were added to plasma independently [(Wun, Blood 79, 430–438 (1992)]. The present work extends the former work and establishes that synergism occurs with homogeneous preparations of FL-TFPI and CT-TFPI. In addition it is shown that FL-TFPI is far more potent than CT-TFPI alone or in combination with heparin.

An unexpected finding of the present work is that the manifestation of maximum FL-TFPI activity and its synergy with heparin was dependent on the weight ratio of the two components and whether the two components were pre-mixed before adding to the plasma.

When a pre-mixed heparin/FL-TFPI complex at a weight ratio below 1.25:1 was added to plasma, the tissue factor-induced clotting time was shorter than when FL-TFPI was added alone. The reason for the depressed activity is not clear, but it is likely due to the neutralization of the positive charges of the carboxyl terminus of the FL-TFPI by heparin. The following results are consistent with this interpretation:

(1) In a dPT assay, 37 fold higher concentrations of CT-TFPI than FL-TFPI are needed to achieve the same extent of clotting time prolongation, suggesting that the highly positively charged carboxy terminus of FL-TFPI is crucial for its activity.

(2) The electrostatic interaction between FL-TFPI and heparin appears very strong and it requires 0.6–1M of NaCl to dissociate the complex. It is likely that few proteins in plasma would be able to displace FL-TFPI from heparin during the clotting assay, and thus the activity remains depressed;

(3) Plasma contains a large number of heparin-binding proteins to compete for binding to heparin, and thus reduces binding of heparin to the carboxyl terminus of FL-TFPI; and (4) Preformed complexes consisting of FL-TFPI and derivatives of heparin with low anticoagulant activity such as N-acetyl heparin and LMWH exhibited activities lower than FL-TFPI alone, suggesting that an unneutralized carboxyl terminus is crucial for FL-TFPI's activity.

All these results directly argue against a 'template' mechanism in which heparin serves to enhance the rate of inhibition of the relevant proteases by FL-TFPI in plasma.

When a pre-mixed heparin/FL-TFPI complex at a weight ratio larger than 1.25:1 was added to plasma, the TF-induced clotting time was equal to or greater than expected from the sum of either agent alone.

The molecular mechanism by which varying the heparin/FL-TFPI ratio effects the switching over from inhibition of FL-TFPI activity by heparin to additive or synergistic action is currently not clear. It is possible that different heparin/FL-TFPI complexes may be formed when the weight ratio changes. Furthermore, additive or synergistic effects were observed only at heparin concentrations that prolong the clotting time by itself. Under this condition, the entire coagulation cascade may become more tightly controlled as the intrinsic and extrinsic pathways are efficiently inhibited by heparin and FL-TFPI, respectively, and thus give rise to a synergistic anticoagulant effect.

The pharmacokinetics of FL-TFPI was found to be very different from that of heparin/FL-TFPI complex. While both can be fitted into a bi-exponential clearance model, the alpha- and beta-phases of clearance are drastically altered. FL-TFPI has a very short $t_{1/2}\alpha$(1.4 min) and a relatively long $t_{1/2}\beta$(92 min) with $AUC_\beta$(92%) dominant.

Heparin/FL-TFPI, in contrast, has a prolonged $t_{1/2}\alpha$(15 min) and a similar $t_{1/2}\beta$(116 min) with $AUC_\alpha$(88%) dominant. The overall clearance is ~2.6 fold faster for FL-TFPI than heparin/FL-TFPI complex. Constant infusion studies confirmed that it is possible to achieve the same steady state level of TFPI in the circulating plasma by infusing 2.6 fold less complex than infusion of the FL-TFPI alone.

The use of heparin/FL-TFPI complexes for treatment of certain thrombotic complications is demonstrated in a rabbit crescentic fibrin-dependent glomerulonephritis model in application Ser. No. 08/661,236, filed concurrently herewith by Tipping and Wun, the disclosure of which is incorporated herein by reference.

It was shown that administration of a clinical dose of heparin did not produce a beneficial effect on the disease process. Neither did the infusion of 10 μg/kg/min of FL-TFPI alone for three days. In contrast, infusion of a clinical dose of heparin in complex with FL-TFPI (heparin/FL-TFPI weight ratio of 1.25:1) such that the rate of infusion was equivalent to 3.3 μg FL-TFPI/kg/min resulted in significantly reduced development of glomerular fibrin deposition, proteinuria, and renal impairment.

Thus, the potential advantages of using heparin/TFPI complex (at weight ratios $\geq$1.25:1 in the treatment of thrombotic complications are three-fold:

(1) It improves the solubility of FL-TFPI;

(2) It reduces the dose requirement of FL-TFPI; and (3) It exerts beneficial effects on certain diseases in which heparin or FL-TFPI alone does not.

TABLE 1

Pharmacokinetic parameters of FL-TFPI and heparin/FL-TFPI complex.

| rabbit | $t_\alpha$ (min) | $t_\beta$ (min) | $V_d$ (ml/kg) | AUC ($\mu$g ml$^{-1}$min$^{-1}$) | % $AUC_\alpha$ | % $AUC_\beta$ | Clearence (ml min$^{-1}$kg$^{-1}$) |
|---|---|---|---|---|---|---|---|
| TFPI#1 | 1.5 | 89 | 118 | 254 | 9.4 | 90.6 | 5.9 |
| TFPI#2 | 1.7 | 96 | 118 | 348 | 7.2 | 92.8 | 4.3 |
| TFPI#3 | 1.0 | 91 | 115 | 219 | 7.9 | 92.1 | 6.8 |
| Mean | 1.4 | 92 | 117 | 274 | 8.2 | 91.8 | 5.7 |
| ±SEM | 0.2 | 2.7 | 1.0 | 47 | 0.8 | 0.8 | 0.9 |
| Hep/TFPI#1 | 15.4 | 99 | 60 | 626 | 86.6 | 13.4 | 2.4 |
| Hep/TFPI#2 | 12.8 | 94 | 49 | 649 | 84.7 | 15.3 | 2.3 |
| Hep/TFPI#3 | 16.6 | 155 | 46 | 837 | 91.7 | 8.3 | 1.8 |
| Mean | 14.9 | 116 | 52 | 704 | 87.7 | 12.3 | 2.2 |
| ±SEM | 1.3 | 24 | 5 | 82 | 2.6 | 2.6 | 0.2 |

The administration of the pre-formed heparin/TFPI complexes to a host or patient in need thereof can be carried out by conventional means, preferably in formulations with pharmaceutically acceptable diluents and carriers. The amount of the heparin/TFPI complex which would normally be administered is primarily dependent on the physical characteristics of the host or patient and the severity of the pathological condition.

The amount to be administered must be an effective amount, that is, an amount which is medically beneficial for inhibiting coagulation or for inhibiting fibrin dependent glomerulonephritis, but which does not present toxic effects which overweigh the advantages which accompany its use. The preferable route is oral or parenteral, e.g. intravenously.

Administration of the heparin/TFPI complexes in solution with conventional aqueous diluents, e.g., physiologic saline, is illustrative. Other suitable formulations of the active heparin/TFPI complex in combination with pharmaceutically acceptable diluents and carriers in therapeutic dosage form can be prepared by reference to general texts in the field such as, e.g., Remington's Pharmaceutical Sciences, Eighteenth Edition, 1990, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. A pre-formed heparin/TFPI complex consisting of a weight ratio of at least 1.25 parts of heparin to one part of Tissue Factor Pathway Inhibitor (TFPI) dissolved in a physiologically acceptable buffer solution.

2. The pre-formed heparin/TFPI complex of claim 1 in which the weight ratio is from 1.25 to about 100 parts of heparin to one part of TFPI.

3. The pre-formed heparin/TFPI complex of claim 1 in which the TFPI is full-length TFPI.

4. The pre-formed heparin/TFPI complex of claim 2 in which the TFPI is full-length TFPI.

5. A method of inhibiting blood coagulation in whole blood plasma of a warm-blooded mammal comprising exogenously administering to said mammal a pre-formed heparin/TFPI complex of claim 1.

6. The method of claim 5 in which the weight ratio of the pre-formed heparin/TFPI complex is from about 1.25 to about 100 parts of heparin to one part of TFPI.

7. The method of claim 5 in which the TFPI is full-length TFPI.

8. The method of claim 6 in which the TFPI is full-length TFPI.

9. The method of claims 5, 6, 7 or 8 in which the exogenous administration of the pre-formed Heparin/TFPI complex is carried out intravenously.

10. The pre-formed heparin/TFPI complex of claim 1 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

11. The pre-formed heparin/TFPI complex of claim 2 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

12. The pre-formed heparin/TFPI complex of claim 3 in which:

(A) the heparin is dissolved in normal physiologic saline,
(B) the TFPI is dissolved in a buffer selected from the group consisting of:
2M urea-saline,
0.2M L-arginine-20 MM phosphate-saline and 5% mannitol-0.1 mM HCl, and
(C) the respective solutions in parts (A) and (B) are mixed to form the soluble heparin/TFPI complex.

13. The pre-formed heparin/TFPI complex of claim 4 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

14. The method of claim 5 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

15. The method of claim 6 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

16. The method of claim 7 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

17. The method of claim 8 in which:

(A) the heparin is dissolved in normal physiologic saline,
(B) the TFPI is dissolved in a buffer selected from the group consisting of:
2M urea-saline,
0.2M L-arginine-20 mM phosphate-saline and 5% mannitol-0.1 mM HCl, and
(C) the respective solutions in parts (A) and (B) are mixed to form the soluble heparin/TFPI complex.

* * * * *